(12) United States Patent
Akinbo et al.

(10) Patent No.: US 7,665,374 B2
(45) Date of Patent: Feb. 23, 2010

(54) SURFACE-COATED SOLID-PHASE MICROEXTRACTION DEVICE

(75) Inventors: Olujide T. Akinbo, Indianapolis, IN (US); Michael J. Samide, Indianapolis, IN (US)

(73) Assignee: Butler University, Indianapolis, IN (US)

( * ) Notice: Subject to any disclaimer, the term of this patent is extended or adjusted under 35 U.S.C. 154(b) by 431 days.

(21) Appl. No.: 11/684,951

(22) Filed: Mar. 12, 2007

(65) Prior Publication Data
US 2007/0209453 A1 Sep. 13, 2007

Related U.S. Application Data

(60) Provisional application No. 60/781,145, filed on Mar. 10, 2006.

(51) Int. Cl.
*G01N 1/22* (2006.01)
(52) U.S. Cl. .................. 73/863.21; 73/863.12

(58) Field of Classification Search ............ None
See application file for complete search history.

(56) References Cited

U.S. PATENT DOCUMENTS

| | | | | |
|---|---|---|---|---|
| 4,596,157 A | * | 6/1986 | Laauwe | 73/864.72 |
| 5,514,341 A | * | 5/1996 | Urata et al. | 422/102 |
| 6,296,410 B1 | * | 10/2001 | Ruizendaal | 401/119 |

* cited by examiner

*Primary Examiner*—Robert R Raevis
(74) *Attorney, Agent, or Firm*—Homer W. Faucett, III; Ice Miller LLP

(57) ABSTRACT

The present application relates to a surface-coated SPME with an extracting tip that resists breaking during analysis. Rather than utilizing a hollow fiber tip, a resilient surface coated rod is utilized. Specifically, several grooves are machined into the tip of the SPME device, allowing an adsorbent material to be retained thereon. The resulting surface coated SPME device is more rugged in laboratory use and allows for testing of analytes in chemical environments that result in failures when using fiber tipped SPME devices.

10 Claims, 9 Drawing Sheets

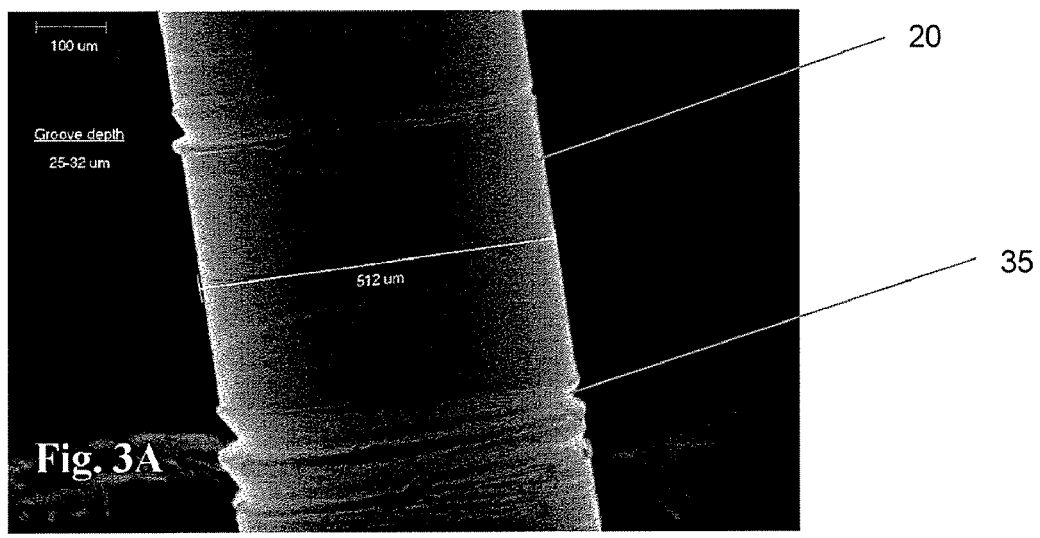
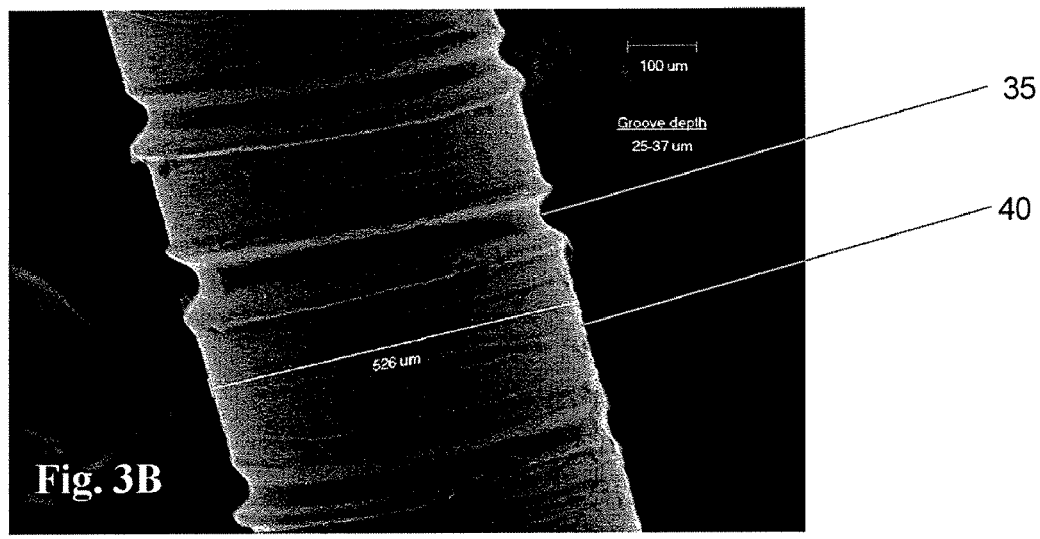

SURFACE-COATED SOLID-PHASE MICROEXTRACTION DEVICE

PRIORITY

This nonprovisional application claims priority to U.S. Provisional Patent Application No. 60/781,145, filed Mar. 10, 2006, which is incorporated herein in its entirety.

BACKGROUND

Solid-phase microextraction ("SPME") is a method of chemical sample preparation and introduction. SPME is typically used for extraction, preconcentration, and introduction of trace level analytes from very dilute solutions into chromatographic separation systems. One advantage of the SPME method is that SME requires no solvent for extraction; the mechanism for extraction and preconcentration is based on physical phenomenon such as adsorption and absorption of analyte by sorbents supported by solid materials such as porous glass fibers. SPME methodology is highly useful for rapid quantitative testing of dilute organic pollutants with the use of little or no hazardous solvents that are used in other similar analytical methods, such as high performance liquid chromatography. Extraction and preconcentration of analytes with SPME can be potentially based on any of a variety of physical mechanisms, including adsorption and absorption, making SPME a versatile analytic tool.

SPME uses a "sorbent" or "adsorbent" material such as carbowax ("CAR"), polydimethylsiloxane ("PDMS"), Carboxan, and divinylbenzene ("DVB"), that can potentially adsorb or absorb a target analyte (the "sorbent" or "adsorbent") from its environment. As noted above, the sorbent is typically supported by a fiber tip (the "tip") that is adhered to a metal base via an adhesive epoxy substance. To extract and preconcentrate a target analyte, the coated tip can be used in either of two ways depending on the volatility of the target analytes. The coated tip is either (1) placed in the headspace of a vial containing the solution of volatile analytes, or (2) dipped into the solution directly in the case of non-volatile analytes. Several comprehensive review articles exist which detail the various methodologies and applications involving SPME technology. See, Hook, et al., Solid-phase microextraction (SPME) for rapid field sampling and analysis by gas chromatography-mass spectrometry (GC-MS); *Trends Anal. Chem.* 21: 534-543 (2002); Snow et al.; Head-space analysis in modern gas chromatography; *Trends Anal. Chem.* 21: 608-617 (2002); Theodoridis et al., Solid-phase microextraction for the analysis of biological samples. *J. Chromatogr. B.* 745: 49-82 (2000); each of which is incorporated by reference herein.

Presently available SPME tips are constructed by impregnating or coating the concentrating material (the "adsorbent") onto a porous silica fiber tip as discussed in U.S. Pat. No. 5,691,206 to Pawliszyn (the "Pawliszyn patent"). The fiber tip is constructed of fused silica fibers similar to those referred to as "optic fibers," with the tip being chemically treated to increase its porosity. The fiber tip is then attached with an adhesive substance (such as an epoxy) or crimped to a metal rod. A sorbent material (which is the active preconcentration agent) is coated onto the fiber.

The glued or crimped junction between the metal rod and the fiber tip is problematic in these devices; it is easily weakened and the coated fiber can break free from the supporting metal rod quite easily. While the chemically treated fiber tip disclosed in the Pawliszyn patent has proven to adhere well to a wide range of adsorbents, the Pawliszyn patent admits that such treated fibers are fragile and require a metal housing (sometimes referred to as a needle) to protect the fiber. Col. 4, lns. 10-20. Further, later changes to improve the rod/fiber interface by crimping the fiber onto a flexible metal support provides better stability, but the tip is still prone to breakage, particularly when working with a solvent that has the ability to swell the coating or dissolve the adhesive.

Therefore, a more rugged SPME tip for supporting the adsorbent without significantly reducing sensitivity of the SPME method would be appreciated. In addition, an SPME tip that eliminates analysis downtime, reduces cost, and facilitates analysis in difficult environments unable to be tested by the prior devices would be appreciated by those in the art.

DESCRIPTION OF THE DRAWINGS

FIG. 3A is a scanning electron micrograph of a groove in a machined tip of the present application formed through the use of razor scoring.

FIG. 3B is a scanning electron micrograph of a groove in a machined tip of the present application formed through the use of razor scoring, and coated with carbowax 20 M.

SUMMARY

Figure 1:
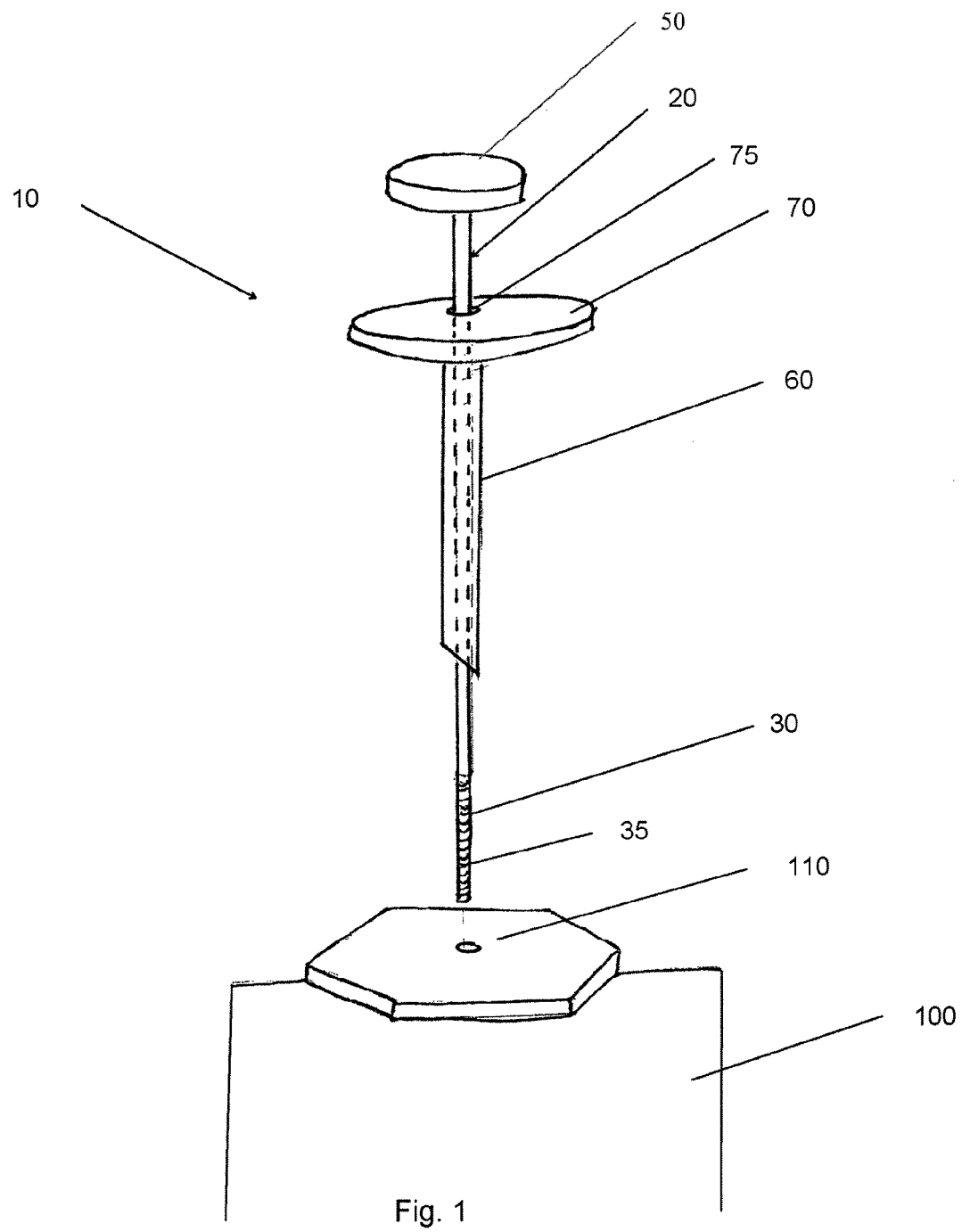
FIG. 1 is a perspective view of a surface coated SPME device according to the present application.

The present application relates to an improved tip for collecting and processing analytes using a solid phase microextraction method.

Specifically, in one embodiment, the present application relates to a device for performing solid phase microextraction of chemicals, with the device comprising a rod with a machined end that can be coated with and retain an adsorbent coating. Additionally, the device comprises a shroud surrounding the rod and in contact with a septum that is operable to maintain a substantially sealed contact between the metallic rod and the shroud, and wherein the rod is operable to move longitudinally within the shroud so that the machined end can be extended outside of the shroud or retracted within the shroud. It will be appreciated that as one option, the machined end has a series of grooves machined into the rod, with the grooves measuring at least about 0.002 inches in depth and no more than about 0.050 inches apart. Another optional embodiment utilizes a series of grooves cut into the rod at the machined end wherein the grooves are at least about 0.004 inches in depth and no more than about 0.030 inches apart.

Another optional embodiment includes an adsorbent coating on the machined end comprising carbowax, polydimethylsiloxane, carboxan, polyurethane, polyacrylate, or divinylbenzene. As another optional embodiment, the device may utilize metal, a plastic, or a ceramic as the rod. Another optional embodiment of abovementioned device includes comprising the rod of stainless steel or aluminum. Optionally, the device of may comprise a rod having a steel core coated with gold or platinum. Further, in another embodiment, polyetheretherketone may be used as all or a portion of the shroud. Finally, The device may be operable to be placed within a gas chromatograph chamber.

Yet another embodiment of the present application relates to a device for performing solid phase microextraction of chemicals, with the device comprising a rod having a grooved end operable to be coated with an adsorbent coating, a shroud surrounding the rod and in contact with a septum operable to maintain a substantially sealed contact between the metallic rod and the shroud, and wherein the rod is operable to move longitudinally within the shroud such that the rod can moved in a manner such that grooved end can be extended outside of the shroud or retraced within the shroud. Finally, the grooved end comprises a series of grooves cut into the rod.

Optionally, the series of grooves cut into the rod are at least about 0.002 inches in depth and are spaced so that there are no less than 20 grooves per inch. Such a grooved machined end can optionally comprises a layer of gold or platinum bonded to the rod. Yet another option includes the grooved end further comprising an adsorbent coating such as an adsorbent including carbowax, polydimethylsiloxane, carboxan, or divinylbenzene.

Yet another optional embodiment includes the series of grooves comprising a plurality of grooves machined into the rod wherein each groove is at least about 0.002 inches in depth and wherein spacing between the grooves results in no less than 30 grooves per inch. Another optional alternative embodiment is made wherein the series of grooves comprises a plurality of grooves machined into the rod and wherein each groove is at least about 0.004 inches in depth and wherein spacing between the grooves results in no less than 20 grooves per inch. In any of the abovementioned embodiments, the rod may optionally comprise steel or aluminum.

Description

The present application relates to an improved solid phase microextraction ("SPME") tip and SPME device, and their method of use and manufacture.

According to one embodiment of the present application as shown in FIG. 1, an SPME device 10 comprises a metal rod 20 having a machined tip 30 operable to receive an adsorbent coating 40 (shown in FIGS. 3B and 4B) and an optional plunger end 50 opposite the machined tip 30. Rod 20 fits within shroud 60, which is typically sized and shaped as a channel or tube operable to allow rod 20 to be placed within shroud 60 when rod 20 is pulled to its retracted position, but short enough to allow machined tip 30 to protrude from shroud when rod 20 is urged to its extended position, as shown in FIG. 1. In one embodiment, a septum 70 having an opening 75 is placed near entry end of shroud 60, and is optionally adhered to or integral with shroud 60.

If septum 70 is integral with or adhered to shroud 60, opening 75 is aligned with the channel or open tube of shroud 60. In practice, septum 70 acts as an interface and seal for rod 20, and allows for maintenance of gas chromatograph pressure when SPME device 10 is placed within a gas chromatograph chamber interface 100 during analysis of an analyte adsorbed or absorbed to adsorbent coating 40. According to one embodiment of the present invention shroud 60 and septum 70 comprise flexible polyetheretherketone (PEEK) polymer, available from Vectrex in West Conshohocken, Pa., which shows little reactivity with most solvents, and can withstand high temperatures. Shroud 60 operates to both cover adsorbent coating 40 of machined end 50 to prevent contamination prior to and after adsorbing a target analyte, and to act as an aid to seal the gas chromatograph chamber 100 when SPME device is inserted therein as shown in FIG. 1.

Figure 4A:
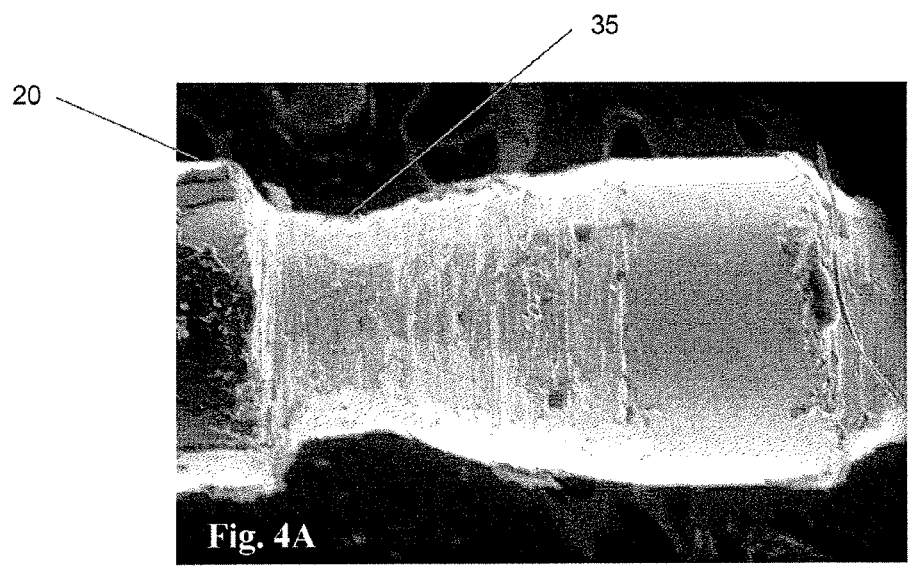
FIG. 4A is a scanning electron micrograph of a groove in a machined tip of the present application formed through a machining process according to the present application.
Figure 4B:
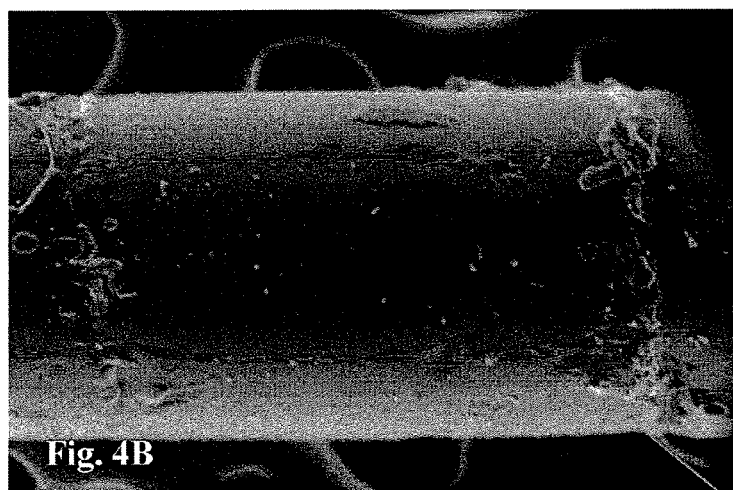
FIG. 4B is a scanning electron micrograph of the groove in a machined tip of FIG. 4A formed through a machining process according to the present application and coated with PDMS.

Metal rod 20 and machined tip 30 can comprise several different metals and alloys such as stainless steel or aluminum, contrary to prior teachings that employ fragile etched silica fibers as the sorbent coating support material. In addition, rod 20 may comprise an underlying structural metal that is coated with another substance, such as gold or platinum, or rod 20 may simply be coated with another metal at machined tip 30. It has been found that carefully machining small grooves radially about metal rod 20 creates a surface to which adsorbent coating 40 may adhere. As shown in FIG. 4A, a scanning electron micrograph of machined tip 30 of rod 20, grooves 35 are machined in the relatively smooth metal rod 20 to provide additional surface area and points for adhesion of adsorbent coating 40. FIG. 4B shows a scanning electron micrograph of one of the machined grooves 35 in the machined tip 30 shown in FIG. 4A after machined tip 30 was coated with the adsorbent coating PDMS, giving the coated tip 30 a filled and consistent appearance with a rough surface.

As can be seen in FIG. 3A, an exemplary embodiment of a tip 30 wherein grooves 35 were produced by using a razor blade or other sharp object to mill grooves in a steel rod, rod 20 has a diameter of approximately 512 μm when uncoated, and approximately 526 μm when coated with adsorbent coating 40. The diameter of machined tip 30 may vary substantially depending upon the application for which the tip is designed, but most gas chromatograph chambers 20 are sized to allow insertion of a tip and/or shroud that is sized between 500 μm to 1000 μm.

As discussed above, grooves 35 may be imparted through the use of razor scoring (FIG. 3A), the use of shallow cutting blades, or by machining (as shown in FIG. 4A). Likewise, surface of tip 30 can be prepared to accept adsorbent coatings 40 by etching tip 30 with acid or other appropriate chemicals. However, it has been found that grooves produced through machining processes result in better performance of SPME device 10 and give rise to an ability to utilize a full range of adsorbent coatings 40 with better sensitivity. Further, it has been found that deeper and more closely spaced grooves 35 in tip 30 result in a tip that is more robust in its ability to accept surface coatings of adsorbent coating 40, and allow several different coatings in various formulations to be made. As such, acceptable results can be obtained by using grooves that are at least about 20 μm through razor scoring of metal rod 20.

However, experimental analysis has indicated that groove depth of at least about 76 μm (about 0.003 inches) and a spacing of no more than about 1270 μm (about 0.05 inches) between grooves 35 provides optimal performance. Further, according to experimental results disclosed below in Example IV, groove spacing of about $10^{-1}$ μm (about 0.004) inches and groove spacing of about 762 μm (about 0.030") between grooves provides results comparable to the commercially available etched fiber optic tip.

EXAMPLE I

Analysis of Ethanol in Water using Razor Scored Surface Coated SPME with Carbowax-20M A. Preparation of Surface Coated SPME Tips A sample surface coated SPME tip according to one embodiment of the present application was prepared to compare the performance with a commercially available SUPELCO® brand fiber tip. The surface-coated SPME device utilized in Example I was manufactured using a 0.50 mm diameter steel rod 20. Rod 20 was prepared by scoring grooves 35 that measured approximately 27 μm-35 μm deep into the rod by placing a razor blade in contact with the rod and rotating the rod under the blade. Each rod was prepared with a different density of grooves to compare performance based upon the number of grooves per unit distance. For each rod, the number of major grooves in a 1.5 cm section of the tip was determined using optical microscopy and a groove density was calculated for each tip. This groove density was used to distinguish each tip during subsequent analyses; tips were created with 3, 8, and 13 grooves/cm (Tip 3, Tip 8, and Tip 13, respectively).

Once machined, the 1.5 cm section of each steel support rod (or tip) was coated using a 10% Carbowax 20M solution in dichloromethane. Once coated, the tips were dried in air. FIGS. 3A and 3B are scanning electron micrographs of an uncoated tip (FIG. 3A) and a coated tip (FIG. 3B) prepared utilizing this method.

B. Preparation of SPME Device

Figure 2:
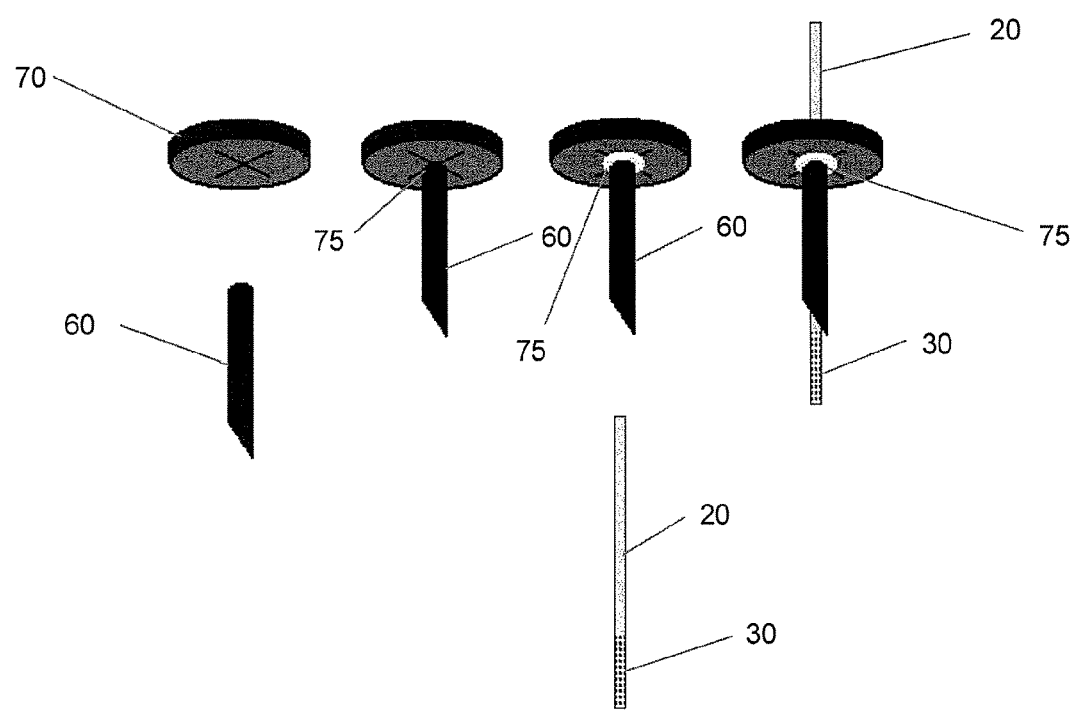
FIG. 2 is a perspective diagram depicting the production of a surface coated SPME device according to the present application.

In order to insert the coated tip into the injector port of gas chromatograph 100, a shroud 60 was utilized. Initial attempts involved the use of a 20 gauge steel syringe needle as shroud 60, but the heat transfer from the heated injector port through the needle to the steel support rod resulted in unfavorable results. Because of the rapid heating, the Carbowax 20M coating melted and dripped from tip 30. In order to prevent the loss of the adsorbent coating, an insulating needle was fashioned using PEEK tubing (1/16" o.d. 0.030" i.d.) described above. As shown in FIG. 2, a 4 to 7 cm length of tubing was used as shroud 60 and a 45° angle was cut into the end to allow for easy penetration of the SPME device into opening 75 of septum 70. Septum 70, also comprising PEEK material was cut to provide an "X" pattern through which shroud 60 could be inserted. Alternatively, a opening 75 could be drilled for insertion of shroud 60. In this instance, shroud 60 was secured to septum 70 through the use of cyanoacrylate adhesive. Coated rod 20 was then inserted into opening 75 of septum 70 and through shroud 60. Septum 70 acts as a seal, allowing the gas chromatograph chamber 100 to maintain pressure through the column during desorption of the analyte into the injector port of the gas chromatograph.

C. Testing of Samples

An Agilent 6890 gas chromatograph equipped with a flame-ionization detector was used for all analyses. Analysis of ethanol (Pharmco, 100%) occurred on a J&W DB Wax column (15 m×0.25 mm×0.25 μm) at a temperature of 50° C. for 3 minutes and increased at 20° C. per minute to 150° C. The gas chromatograph injector port was held at a constant temperature of 80° C. (splitless) and the detector was held at 250° C.

To evaluate the sensitivity and linearity and accuracy of the surface-coated SPME, a calibration curve was constructed by performing the headspace analysis of aqueous ethanol solutions in the concentration range of 1 to 15% (v/v). Each SPME (commercially available and surface-coated) was exposed to the vapors in the headspace above the sample for a pre-determined length of time (1 minute for the commercially available and 8 minutes for the surface-coated SPME according to the present application) and analysis of the adsorbed material was accomplished by gas chromatography. The difference in exposure time for the commercially available tip and the surface-coated SPME tips according to the present application relates to the optimization of the conditions required for both tips. As can be seen, the razor-scored tips were required to be exposed for a longer period than the commercially available SPME tip for analysis.

D. Results

Figure 5A:
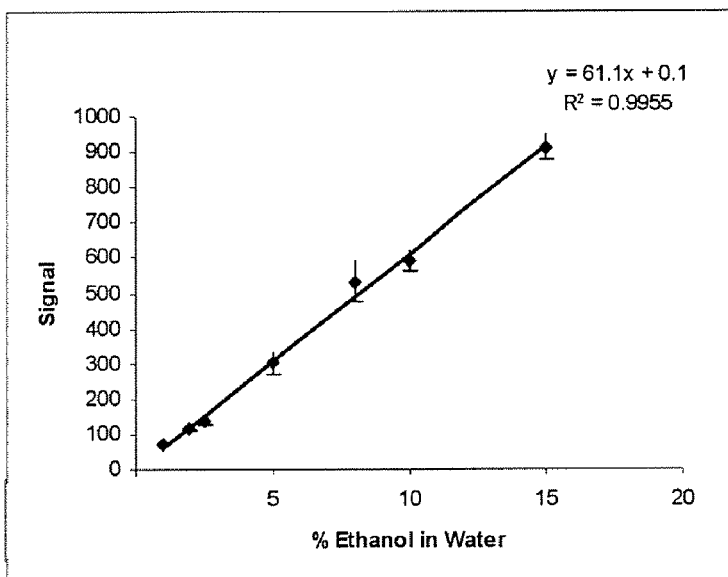
FIG. 5A is a diagram representing the sensitivity of a commercially available SPME tip in detecting ethanol concentration in water.
Figure 5B:
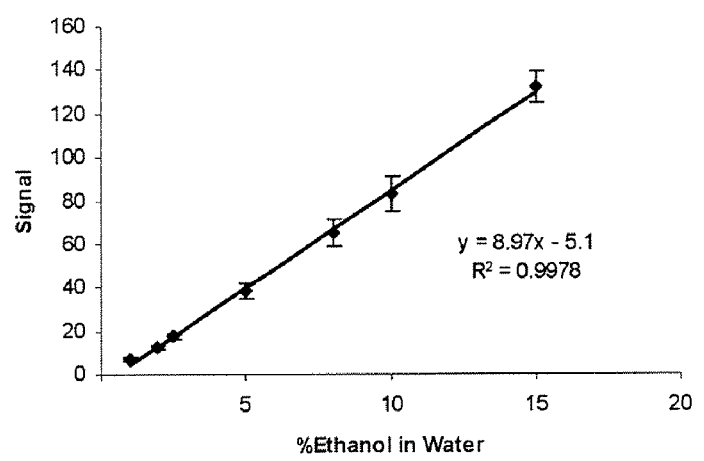
FIG. 5B is a diagram representing the sensitivity of an razor scored SPME tip in detecting ethanol concentration in water
Figure 5C:
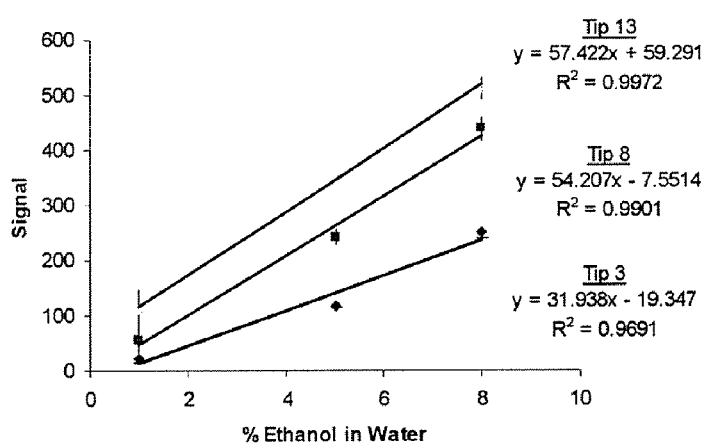
FIG. 5C is a diagram representing the sensitivity of three razor machined surface coated SPME tips having varying concentrations of grooves in detecting ethanol concentration in water.

Calibration curves for the gas chromatograph analysis of 1 to 15% solutions of ethanol (v/v) in water are presented in FIGS. 5A-5C. The slope of each curve represents the sensitivity of the tip tested, providing comparison values between the various tips shown. The curve represented in FIG. 5A shows the data obtained using the commercially available impregnated-fiber SPME. A linear response was obtained and a calibration sensitivity of 61.1 was calculated. The curve represented in FIG. 5B represents the results obtained from the preliminary study of a surface-coated SPME, where a steel rod was manually scratched with a razor blade with no measurements of the depth or density of the grooves. As can be seen, the sensitivity of this device is low. The curve represented by FIG. 5C depicts the response of three different surface-coated tips prepared by razor scoring as described above and comparing the effects of groove density on sensitivity performance. In all cases, linearity is displayed over a range of 1 to 8% ethanol in water. Tip 3, scored to 3 grooves per cm, shows a sensitivity of approximately 31.9 area count per % ethanol less than the commercial tip. However, both Tip 8 (8 grooves per cm) and Tip 13 (13 grooves per cm) show a sensitivity of 54.2 and 57.4, which approaches the sensitivity of the commercially available tip while eliminating the brittle nature of the commercial tip.

EXAMPLE II

Analysis of Ethanol in Water using Precision Machined Surface Coated SPME with Carbowax-20M Coating A. Preparation of Surface Coated SPME Tips Two sample surface coated SPME tip according to one embodiment of the present application were prepared to compare reproducibility of sensitivity when machined tips are used. The surface-coated SPME device utilized in Example II was manufactured using a 0.50 mm diameter steel rod 20. Rod 20 was prepared by machining grooves 35 that measured approximately 101 μm deep on a standard lathe. Each groove 35 was made by placing a rotary cutting device (such as a Dremel® high speed rotary tool) outfitted with a diamond-coated wafering blade (a 0.006 inch thick blade available from Buehler) mounted between two 2 inch aluminum washers for stability. The rotary tool was then mounted in a milling machine equipped with a digital micrometer to allow accurate movement in depth of cut and distance between cuts. The spinning diamond blade was lowered into rod 20 as the lathe would spin rod 20 about its longitudinal axis twice, resulting in a single axial groove around rod 20. The spinning diamond blade was then raised above rod 20, moved longitudinally a predetermined distance, and lowered again to create a 0.004 inch deep groove in rod 20, with each groove resembling that shown by the scanning electron micrograph shown in FIG. 4A. Spacing was chosen between 0.030 inches and 0.035 inches between grooves. The machined tips were then coated with PDMS and produced a very consistent coating as shown by the scanning electron micrograph shown in FIG. 4B.

B. Testing of Samples

An Agilent 6890 gas chromatograph equipped with a flame-ionization detector was used for all analyses. Analysis of ethanol (Pharmco, 100%) occurred on a J&W DB Wax column (15 m×0.25 mm×0.25 μm) at a temperature of 50° C. for 3 minutes and increased at 20° C. per minute to 150° C. The gas chromatograph injector port was held at a constant temperature of 80° C. (splitless) and the detector was held at 250° C.

According to one embodiment of the present application SPME tips were prepared according to the procedures outlined in Example I. In particular, all tips in this Example II were created using a groove depth of about 0.004 inches and groove spacing of about 0.035 inches between grooves. Analysis of aqueous ethanol solutions was performed using two precision machined tips coated with Carbowax 20M. For each solution, the device was exposed to the headspace for 2 minutes and allowed to desorb in an 80° C. injector for 2 minutes.

Figure 6:
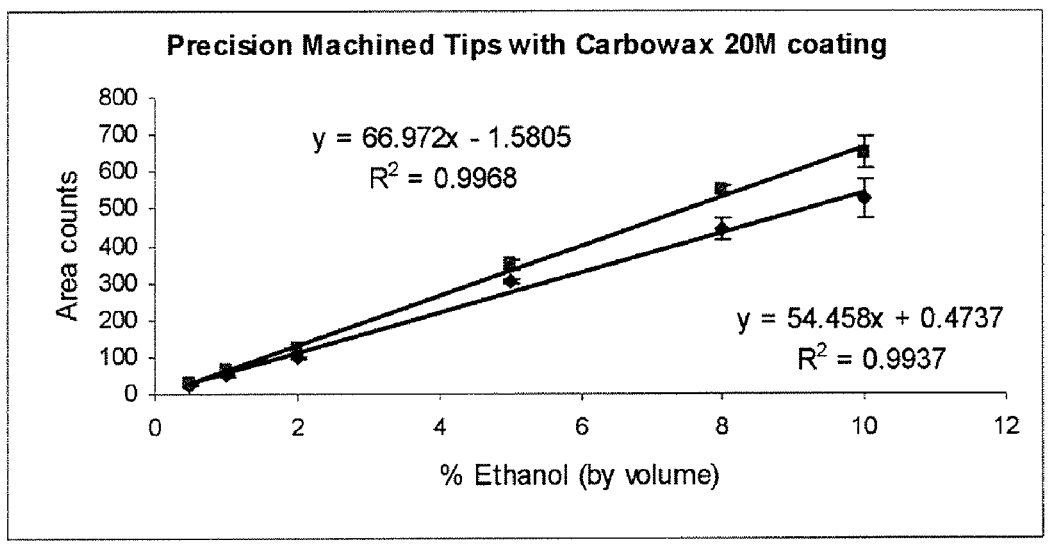
FIG. 6 is a diagram representing the sensitivity of two machined surface coated SPME tips in detecting ethanol concentration in water.

An Agilent 6890 GC with splitless injection, a J&W Scientific DB-Wax column (15 m×0.25 mm×0.25 μm), and an FID detector was employed for this analysis. The column temperature was held constant at 50° C. As can be seen in FIG. 6, the sensitivities (slope of the calibration line) of the devices are nearly identical, with a small deviation as a result of variations in the coating of the adsorbent onto the machined surface. Further, a chromatogram of headspace sampling of 100 ppm aqueous ethanol solution, showed the Carbowax-coated, precision machined grooved tip to produce a signal to noise ("S/N") ratio of approximately 72, well above the level necessary for quantitation (S/N>30). The results were limited to the analysis of ethanol due to the thermal properties of Carbowax. A solid at room temperature, Carbowax 20M becomes a liquid at approximately 78° C. and drips off the device if exposed to temperatures above 80° C. in an injector port.

EXAMPLE III

Analysis of BTEX in Hexane Using Precision Machined Surface Coated SPME with Polydimethylsiloxane Coating A test was run to compare the efficacy of a tip according to one embodiment of the present application utilizing a metal surface coated SPME tip as described in Example II. However, two separate surface coated SPME tips were created to identical specifications, utilizing PDMS as the adsorbent coating and machining the grooves to approximately 0.004 inches and at a spacing of about 0.030 inches. Analysis of a 3220 ppm each of toluene, ethylbenzene, and p-xylene (TEX) solution was accomplished using two different machined PDMS coated SPME devices. Benzene, the other component of the typically analyzed BTEX solution could not be analyzed due to co-elution (as a shoulder) with the solvent, hexane. As will be noted in example IV, neither the commercially available device nor the surface coated SPME according to the present application were able to quantify benzene in this application. Analysis was performed using an Agilent 6890 GC with splitless injection, an Agilent HP-5 column (30 m×0.32 mm×0.25 μm), and an FID detector.

Figure 7:
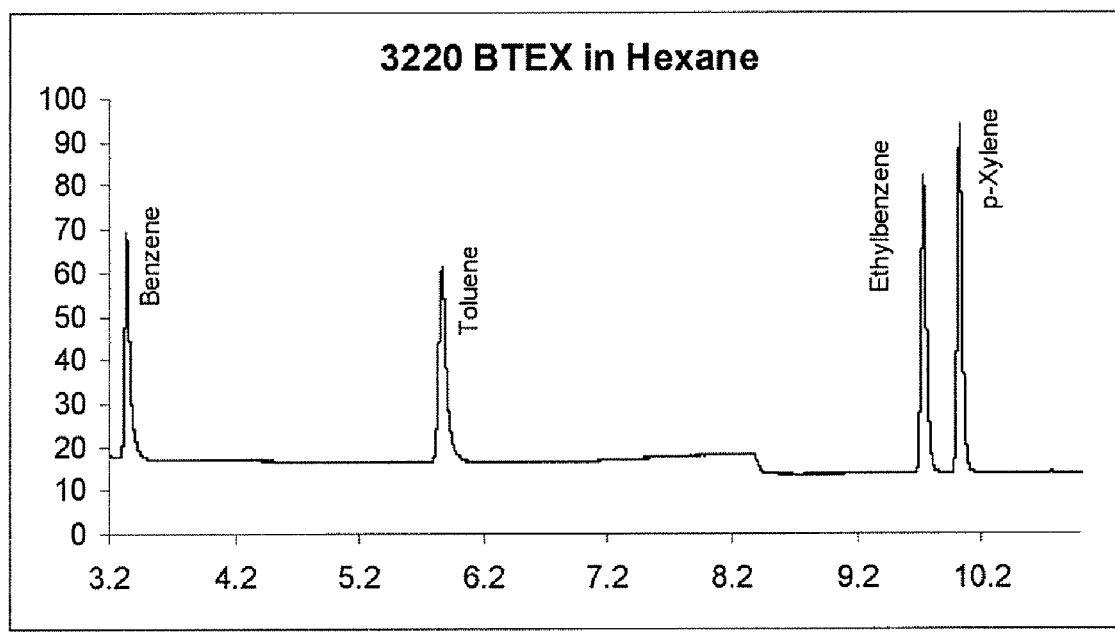
FIG. 7 is a chromatogram representing headspace sampling of 3220 ppm each of benzene, toluene, ethylbenzene, and p-xylene (BTEX) in hexane with exposure time of 2 min.

To highlight the robust nature of the precision machined device, during Example III, one machined device was accidentally dropped and collected a large amount of dust prior to analysis. It was simply wiped off, the sampling device baked, and then used for analyses. Excellent results were still obtained with this rod, consistent with the other machined surface coated SPME device, and showing the excellent reproducibility of the results from the surface coated SPME device according to one embodiment of the present application. FIG. 7 displays the chromatogram of headspace sampling of 3220 ppm each of toluene, ethylbenzene, and p-xylene (BTEX) in hexane with exposure time of 2 min.

Figure 8:
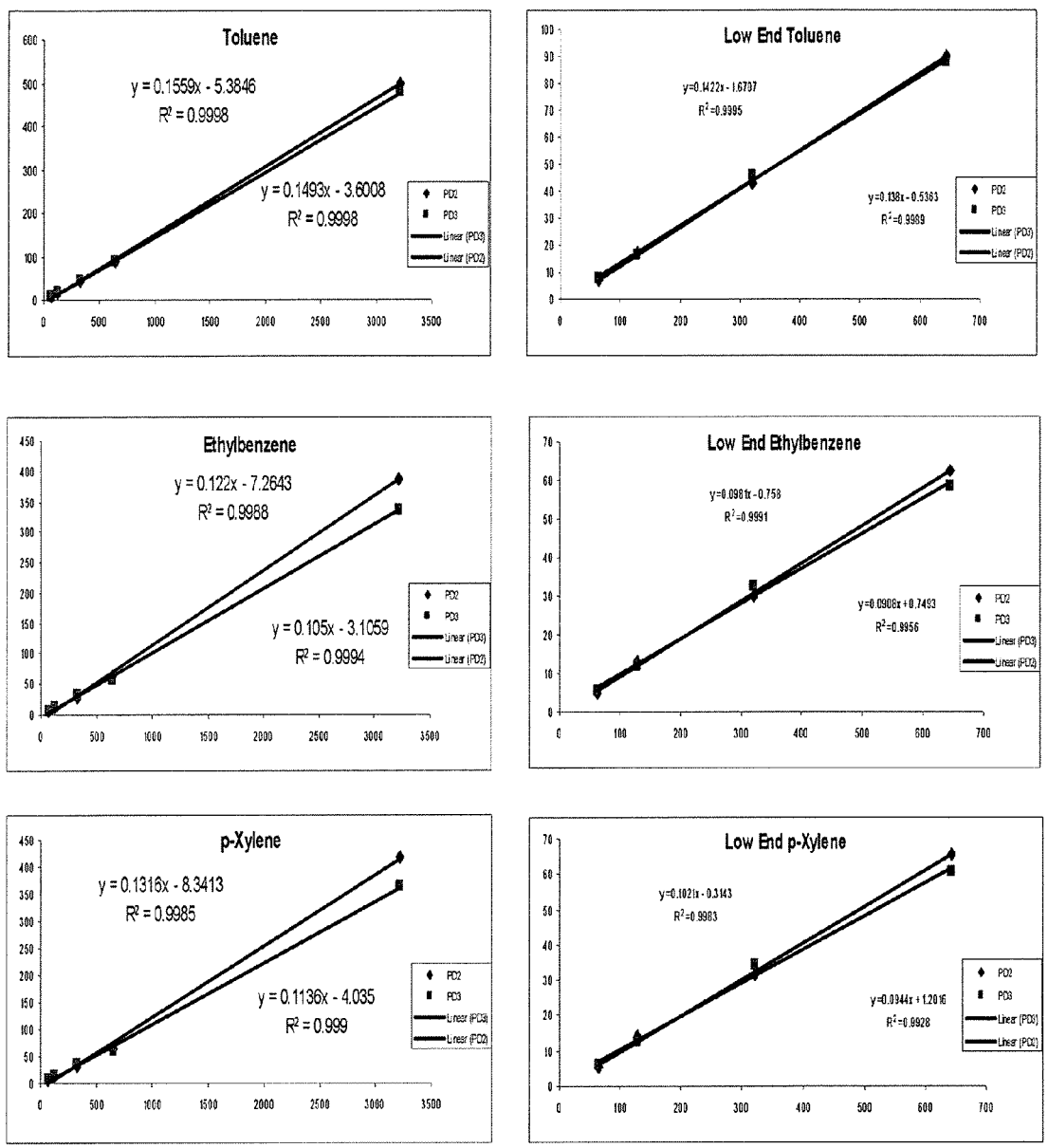
FIG. 8 is a series of diagrams representing the sensitivity of two machined surface coated SPME tips in detecting noted compounds in hexane.

When compared to a commercially available fiber tipped SPME device, Example III highlights the robust nature of the surface coated SPME device. An attempt to use the commercially available tip for the analysis of the BTEX solution in hexane was not feasible, as the hexane vapor caused the swelling of the PDMS and weakening of the glue holding the fiber to the metal support. This resulted in the extraction tip falling off of two different commercially available tips within a 5 minute time window. Therefore, sensitivity was not able to be compared with the commercially available SPME tip because the commercial tip failed while the tips prepared according to the present application performed consistently, even when dropped prior to use. The calibration plots observed for the remaining samples are shown in FIG. 8 where PD2 and PD3 represent the two separate, identically machined surface coated SPME tips compared to one another.

EXAMPLE IV

Analysis of BTEX in Methanol Using Precision Machined Surface Coated SPME with Polydimethylsiloxane Coating Due to the failure of the commercially available tip when used to quantify BTEX in hexane, new known samples for benzene, toluene, ethylbenzene and o-xylene (2762 to 55 ppm) in methanol were prepared for comparative performance between the surface coated SPME device and the commercially available SPME tip. In each case, the calibration sensitivity for the surface coated SPME tip according to the present application A. Preparation of Surface Coated SPME Tips A sample surface coated SPME tip according to one embodiment of the present application was prepared to compare the performance of a tip with precisely machined grooves with a commercially available SUPELCO® brand fiber tip. The surface-coated SPME devices ("scSPME") utilized in Example IV were manufactured identically to that described in Example III.

B. Testing of Samples

Figure 9:
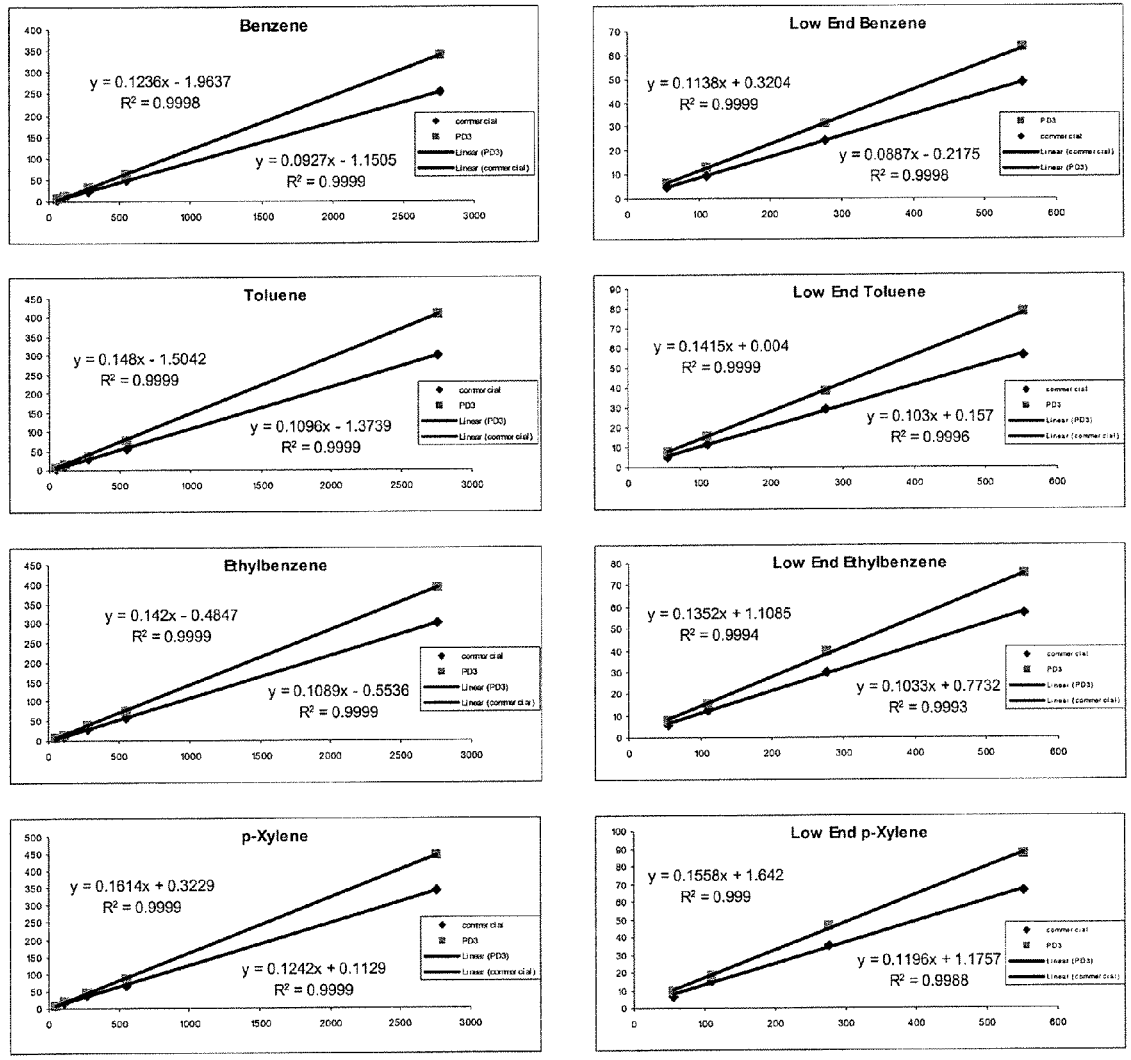
FIG. 9 is a series of diagrams representing the sensitivity of a machined surface coated SPME tip in comparison to a commercial SPME tip in detecting noted compounds in methanol.

An Agilent 6890 gas chromatograph equipped with a flame-ionization detector was used for all analyses. Two separate surface coated SPME tips were created to identical specifications, utilizing PDMS as the adsorbent coating and machining the grooves to approximately 0.004 inches and at a spacing of about 0.030 inches. Analysis of a 3220 ppm BTEX solution (as described above) was accomplished using two different machined PDMS coated SPME devices. Accuracy of the each SPME sampling device was established by analyzing a gasoline sample reference solution purchased from NIST (SRM#2297). Monitored were toluene, ethylbenzene, and o-xylene. Benzene co-elutes with another component of the mixture and could not be quantified. The precision (% RSD) and the accuracy (% difference from the known) for each device were comparable. Analysis was performed using an Agilent 6890 gas chromatograph with splitless injection, an Agilent HP-5 column (30 m×0.32 mm×0.25 μm), and an FID detector. FIG. 9 displays the results of the calibration tests, with PDMS-coated surface coated SPME (■) according to the present application and a commercially available 100 μm PDMS SPME (♦). In both Table 1 and FIG. 9, the slope of each curve is represented in the y=mx+b (slope intercept form) where y=the sensitivity of each device.

As can be seen from FIG. 9 and Table 1 below, the surface coated SPME performed with substantially similar sensitivity in each analyte, and displays substantially more resilience in laboratory use as shown in example III above. Table 1 below represents the comparison of the sensitivity for both the commercial tip and the surface coated SPME. As noted above, the sensitivity for the surface coated SPME was comparable to the commercial tip.

TABLE 1

|  | Commercial | Precision Machined |
| --- | --- | --- |
| Benzene | y = 0.0927x − 1.1505 | y = 0.1236x − 1.9637 |
| Toluene | y = 0.1096x − 1.3739 | y = 0.148x − 1.5042 |
| Ethylbenzene | y = 0.1089x − 0.5536 | y = 0.142x − 0.4847 |
| o-Xylene | y = 0.1242x + 0.1129 | y = 0.1614x + 0.3229 |

$^a$in all cases, $R^2$ values ranged from 0.9998 to 0.9999

Furthermore, as can be seen in the results in Table 2 below, when both the commercially available tips and the surface coated SPME tip according to one embodiment of the present application are compared with regard to their ability to quantify the concentrations of the known analytes toluene, ethylbenezene, and o-xylene, the both tips performed comparably. The percentage shown below in table 2 represent the amount measured in compared to the known concentration. In each instance the surface coated SPME performed within 3% of the commercially available tip, and was more accurate in two of the three tests. For the purposes of Table 2, 97% accuracy indicates a predicted concentration what was 3% below the actual, and 115% indicates a concentration that was 15% above the actual.

TABLE 2

|  | Toluene | Ethylbenzene | o-Xylene |
| --- | --- | --- | --- |
| PDMS scSPME (% accuracy) | 97% | 115% | 104% |
| Commercial PDMS tip (% accuracy) | 99.5 | 117% | 107% |

It will be appreciated that the above is simply an exemplary embodiment of the present invention. Several variations and changes will be readily apparent to one of ordinary skill in the art, and are included within the scope of this application. For example, the scSPME may be made of various different materials, including metals other than stainless steel, plastics, ceramics, and various other materials in variable shapes and sizes as deemed appropriate for the sample and application of the scSPME. Further, additional adsorbent materials may be used, such as those used in liquid chromatography.

What is claimed is:

1. A device for performing solid phase microextraction of chemicals comprising:
    a. a rod having a grooved end operable to be coated with an adsorbent coating;
    b. a shroud surrounding the rod and in contact with a septum operable to maintain a substantially sealed contact between the metallic rod and the shroud;
    c. wherein the rod is operable to move longitudinally within the shroud such that the rod can moved in a manner such that grooved end can be extended outside of the shroud or retraced within the shroud;
    d. and wherein the grooved end comprises a series of grooves cut into the rod, wherein the series of grooves comprises a plurality of grooves machined into the rod and wherein each groove is at least about 0.002 inches in depth and wherein spacing between the grooves results in no less than 20 grooves per inch.

2. The device of claim 1, wherein the grooved end further comprises a layer of gold or platinum bonded to the rod.

3. The device of claim 1, wherein the grooved end further comprises an adsorbent coating comprising carbowax, polydimethylsiloxane, carboxan, or divinylbenzene.

4. The device of claim 1, wherein the series of grooves comprises a plurality of grooves machined into the rod and wherein each groove is at least about 0.002 inches in depth and wherein spacing between the grooves results in no less than 30 grooves per inch.

5. The device of claim 1, wherein the series of grooves comprises a plurality of grooves machined into the rod and wherein each groove is at least about 0.004 inches in depth and wherein spacing between the grooves results in no less than 20 grooves per inch.

6. The device of claim 1, wherein the rod comprises one or more of the group consisting of steel and aluminum.

7. A device for performing solid phase microextraction of chemicals comprising:
    a. a rod having a grooved end operable to be coated with an adsorbent coating;
    b. a shroud surrounding the rod and in contact with a septum operable to maintain a substantially sealed contact between the metallic rod and the shroud;
    c. wherein the rod is operable to move longitudinally within the shroud such that the rod can moved in a manner such that grooved end can be extended outside of the shroud or retraced within the shroud;
    d. and wherein the grooved end comprises a series of grooves cut into the rod such that each groove is at least about 0.004 inches in depth and wherein spacing between the grooves results in no less than 20 grooves per inch.

8. The device of claim 7, wherein the machined end comprises a series of grooves machined into the rod, and wherein the grooves are at least about 0.002 inches in depth and no more than about 0.050 inches apart.

9. The device of claim 7, wherein the machined end comprises a series of grooves cut into the rod, and wherein the grooves are at least about 0.004 inches in depth and no more than about 0.030 inches apart.

10. The device of claim 7, wherein the metallic rod comprises a steel core coated with gold or platinum.

* * * * *